United States Patent [19]

Goldberg

[11] Patent Number: 4,511,661
[45] Date of Patent: Apr. 16, 1985

[54] ATCC HB8116 AND ITS MONOCLONAL ANTI-H-Y ANTIBODY, HYCLONALAN

[75] Inventor: Ellen H. Goldberg, Albuquerque, N. Mex.

[73] Assignee: University Patents, Inc., Norwalk, Conn.

[21] Appl. No.: 567,395

[22] Filed: Dec. 30, 1983

Related U.S. Application Data

[63] Continuation-in-part of Ser. No. 359,707, Mar. 19, 1982, abandoned.

[51] Int. Cl.$^3$ .................... G01N 33/54; G01N 33/58; C12N 15/00
[52] U.S. Cl. .............................. 436/503; 260/112 R; 935/104; 935/108; 935/110; 435/4; 435/7; 435/29; 435/68; 435/172.2; 435/240; 435/948; 436/501; 436/510; 436/518; 436/519; 436/547; 436/815; 436/821; 436/824; 436/548
[58] Field of Search ............... 436/501, 547, 548, 503, 436/811, 815, 824, 906, 510, 518, 519; 435/2, 68, 70, 172, 240, 241, 804, 948, 4, 7, 29; 424/9, 85, 177; 260/112 R; 935/104, 108, 110

[56] References Cited

U.S. PATENT DOCUMENTS

| | | | |
|---|---|---|---|
| 4,191,749 | 3/1980 | Bryant | 424/105 |
| 4,423,147 | 12/1983 | Secher | 435/68 |
| 4,448,767 | 5/1984 | Bryant | 424/85 |

OTHER PUBLICATIONS

Savikurki, H. et al., Human Genetics, vol. 65, pp. 190–194 (1983).
White, K. L. et al., Theriogenology, vol. 19(5), pp. 701–705.
Isahakia, M. et al., Fed. Proc. Amer. Soc. Exp. Biol., vol. 42(3), p. 434, abstract 830 (3-1983).
Gore–Langton, R. E. et al., Cell, vol. 32, pp. 289–301 (1-1983).
Gaunt I. J., Develop. Biology, vol. 89, pp. 92–100 (1-1982).
Myles, D. G. et al., Cell, vol. 23, pp. 433–439, (2-1981).
Bechtol, K. B. et al., Proc. Natl. Acad. Sci. USA, vol. 76(1), pp. 363–367 (1-1979).
Tokuda, S. et al., Nature, vol. 267(5610), p. 433–434 (6-1977).
Bechtol, K. B. et al., Amer. Soc. Cell Biol./J. Cell Biol., vol. 79, p. 22A (11-1978).
Goldberg, et al., "Serological Demonstration of H–Y (Male) Antigen on Mouse Sperm", Nature, 232: 478 (1971).
Kohler, et al., "Derivation of Specific Anti–Body Producing Tissue Culture and Tumor Cells by Cell Fusion", Nature, 256: 495 (1975).
Koo, et al., "Application of Monoclonal Anti–H–Y Antibody for Human H–Y Typing", Human Genetics, 57: 64–67 (1981).
Krco, et al., "H–Y (Male) Antigen. Detection on Eight--Cell Mouse Embryos", Science, 193: 1134–1135 (1976).
Oi, et al., pp. 351–372 in "Immunoglobulin Producing Hybrid", Mishell, et al. (eds.), Selected Methods in Cellular Immunology, San Francisco: W. H. Freeman Publishing, 1979.
Sevier, et al., Clin. Chem., 27(1): 1797–1806 (1981).
Wachtel, et al., "Serologic Detection of a Y–Linked Gene in XX Males and XX True Hermaphrodites", New England J. Med., 295: 750–754 (1976).
Wachtel, et al., "H–Y Antigen in Gonadal Differentiation", in Mechanism of Sex Differentiation in Animals and Man (Edwards, et al., editors), Academic Press, London, 1981.

Primary Examiner—Christine M. Nucker
Assistant Examiner—M. Moskowitz
Attorney, Agent, or Firm—Marshall, O'Toole, Gerstein, Murray & Bicknell

[57] ABSTRACT

Hybridoma tumor cell line A.T.C.C. No. HB8116. An anti-H-Y antigen monoclonal antibody substance, "Hyclonalan," produced by said cell line. Use of Hyclonalan in immunoselection methodology.

12 Claims, No Drawings

ATCC HB8116 AND ITS MONOCLONAL ANTI-H-Y ANTIBODY, HYCLONALAN

The invention described herein was made in the course of or under a grant or award from the Department of Health and Human Services.

This is a continuation-in-part of my prior co-pending U.S. patent application Ser. No. 359,707, filed Mar. 19, 1982, now abondoned.

BACKGROUND OF THE INVENTION

The present invention relates generally to materials and methods for use in immunological procedures for selection and differentiation of mammalian male and female cells. More specifically, the invention relates to a monoclonal anti-H-Y antibody, Hyclonalan, produced by a novel tumor cell line ATCC HB8116 and to uses of Hyclonalan in sex immunoselection procedures.

Sex immunoselection allows the separation and identification of male from female cells according to immunological reactions of antibodies specific for antigens on the cell surface. Such immunological reactions could mediate sex differentiation, for example, in a pool of embryos supplied by a female animal, or in a pool of X- and Y-bearing spermatozoa from a male animal. Gender-differentiated embryos or sperm may thereafter be utilized for embryo implantation or artificial insemination of the same or analogous species surrogate females for the preselection of the desired sex of the offspring.

As one example, in the cattle industry, methods for sex immunoselection could be of vital use in upgrading the nutritional characteristics and quantities of cattle raised to supply food and milk. While a cow of reproductive age will normally give birth to only one calf a year, which may be either a male or a female, accurate techniques of immunoselection could allow the birth of many genetically superior calves of a single sex as offspring of one genetically desirable cow. This could be accomplished by subjecting a group of hormonally induced ova from the genetically desirable cow either to fertilization and embryo immunoselection or to artificial insemination by sex-preselected sperm. Embryos thus obtained (e.g., all females) may be implanted into the uteri of surrogates and thereby the desirable genetic characteristics of the parent animals can be propagated with much greater frequency than is possible in nature. The ability to increase the reproductive capacity of genetically prized animals, especially dairy cattle, may be a key to solving the hunger problem which exists in many countries today due to insufficient number of meat-producers.

These technologies also show great promise in increasing the chances for survival of many endangered species. Animal experiments with interspecies embryo transfer have already shown that such techniques may ultimately prove successful in multiplying the flagging numbers of some endangered species of mammals by implanting sex-preselected, genetically desirable embryos from an endangered species into an analogous species surrogate.

In addition, sex immunoselection procedures are also directed at detection of microcellular sex determinants. In individuals with ambiguous gender development, such techniques are utilized to identify abnormal sex chromosome constitutions, particularly in human fibroblast cells.

Current investigation involves immunological techniques to detect the H-Y antigen, the cell surface component found on the male cells of all mammals. The locus of at least one of the genes responsible for H-Y expression is on the Y chromosome, and has been shown to be cross-reactive among numerous species ranging from fish to man. It has been proposed that the H-Y antigen may be the primary sex determinant and possibly the longsought inducer of testicular development in mammals. (Wachtel, et al., 1975; Wachtel and Koo, 1980); Koo, et al., "Application of Monoclonal Anti-H-Y Antibody for Human H-Y Typing," *Human Genetics*, 57: 64–67 (1981).

One of the limitations in current serological and immunological techniques used to detect the H-Y antigen on male cells, including those cells forming Y-bearing spermatozoa and male embryos is the source of antiserum. Antiserum is conventionally produced by injecting the antigen of interest into an immunologically responsive laboratory animal such as a mouse or rat and subsequently preparing antiserum from the blood of the animal, which will contain a mixture of antibodies developed against the antigen together with other antibody substances.

For example, Bryant, U.S. Pat. No. 4,191,749, granted Mar. 4, 1980, discloses a separation scheme for male- and female-determining spermatozoa utilizing a male-specific antibody. The antibody of this reference is prepared from the serum of female rabbits hyperimmunized with male rabbit epidermal cells. The antiserum, which must be complement inactivated, is "purified" by being repeatedly absorbed with washed female rabbit spleen cells and fractionated by agarose gel filtration to obtain the Immunoglobulin G (IgG) antiserum fraction.

Despite current scientific dispute concerning the presence of the H-Y antigen in haploid expression on the surface of spermatozoa, theoretically, X-bearing sperm will elute out of a column in which Bryant's Immunoglobulin G antiserum is coupled with solid phase immunosorbent material, while the Y-bearing sperm attach to the antiserum on the column. The Y-bearing sperm are then eluted out of the column separately with more antiserum solution in accordance with the principles of competitive binding.

Such conventionally-produced H-Y antiserum, although it contains H-Y antibody substances, is usually low-titered and contaminated with heteroantibody which will react with male and female cells of other species due to species-specific cell surface components which are not related to the H-Y antigen. Therefore clinical assays using the H-Y antiserum to detect the H-Y antigen on male cells or aid in separating male embryos and Y-bearing spermatozoa from female embryos and X-bearing spermatozoa will often yield ambiguous and inaccurate results in embryo transferral and fertilization experiments.

This ambiguity in anti-H-Y antiserum is also disadvantageous when used in serologic procedures for the detection of H-Y antigen expression in patients (both animal and human) that demonstrate ambiguous sexual development (hermaphroditic differentiation) or other physical conditions caused by genetic aberrancies in the sex chromosomes. Hermaphroditic differentiation is believed to be caused by the presence of Y-chromosome material as an intact Y chromosome in a mosaic cell line, as a minute part of extra material attached to an X chromosome or as an autosome. Because the chromosome segments and genes which form them are so small, the usual cytological assays cannot always detect them. Serological detection of H-Y antigen expression of these chromosome segments and genes is considered the best evidence of these genotypic abnormalities. However, the serological assays are only as precise in locating the genetic abnormality as is the anti-H-Y antiserum available for use. Wachtel, et al., "Serologic Detection of a Y-Linked Gene in XX Males and XX True Hermaphrodites," *New England J. Med.*, 295: 750-754 (1976).

Researchers in this field have therefore turned to hybridoma techniques to produce tumor cell lines which will manufacture highly specific monoclonal H-Y antibody. Techniques used for the production of monoclonal antibody are well known in the art, and can be found described in Oi, V. T. and L. A. Herzenberg, "Immunoglobulin Producing Hybrid," Mishell, B. B. and S. M. Shiigi (eds.), *Selected Methods in Cellular Immunology*. San Francisco: W. H. Freeman Publishing, 1979. Lymphocytes removed from the spleen of an animal previously injected with the antigen of interest are allowed to fuse with myeloma cells in the presence of polyethylene glycol or a similar fusogen. Thousands of "hybrid" myeloma cells are produced from the fusion. The supernatant from growth of each "hybridoma" cell culture is tested for the presence of the desired antibody activity. When such activity is found in the supernatant of one cell culture, it is cloned by limiting dilutions, and the clones produced are individually assayed for supernatant activity.

To date, monoclonal antibody methodologies have produced monoclonal anti-H-Y antibodies of widely varying specificities and physiological characteristics. An H-Y antibody less than highly specific, however, will not provide an accurate detection of solely the H-Y antigen cell surface which will enable identification and separation of male from female cells and accurate prediction of the results of sex immunoselection techniques, or locate fragments of Y chromosomes in cells of patients with abnormal sex chromosome constitutions.

There exists, therefore, a substantial need for a highly specific monoclonal H-Y antibody to improve the accuracy of sex immunoselection of cells for purposes of artificial insemination and embryo transferral (particularly in the areas of upgrading animal herds and increasing the populations of endangered mammalian species) and for identification of genetic abnormalities.

Specifically incorporated by reference herein for the purposes of indicating the background of the invention and illustrating the state of the art are the following publications:

1. Goldberg, et al., "Serological Demonstration of H-Y (Male) Antigen on Mouse Sperm," *Nature*, 232: 478 (1971);

2. Kohler, G. and Milstein, C., "Derivation of Specific Anti-Body Producing Tissue Culture and Tumor Cells by Cell Fusion," *Nature*, 256: 495 (1975);

3. Koo, et al., "Application of Monoclonal Anti-H-Y Antibody for Human H-Y Typing," *Human Genetics*, 57: 64-67 (1981);

4. Krco, C. J., and Goldberg, E. H., "H-Y (Male) Antigen. Detection on Eight-Cell Mouse Embryos," *Science*, 193: 1134-1135 (1976);

5. Oi, V. T. and L. A. Herzenberg, pp. 351-372 in "Immunoglobulin Producing Hybrid," Mishell, B. B. and S. M. Shiigi (eds.), *Selected Methods in Cellular Immunology*. San Francisco: W. H. Freeman Publishing, 1979; and 6. Wachtel, et al., "Serologic Detection of a Y-Linked Gene in XX Males and XX True Hermaphrodites," *New England J. Med.*, 295: 750-754 (1976).

BRIEF SUMMARY

The present invention provides a new mouse-mouse hybridoma cell line, ATCC HB8116, which provides as a component of the supernatant of its growth the highly specific monoclonal H-Y antibody, Hyclonalan. Cell line ATCC HB8116 was deposited in the American Type Culture Collection 12301 Parklawn Drive, Rockville, Md. 20852, a recognized public depository for strains of microorganisms on Feb. 24, 1982. The present invention provides for the use of Hyclonalan in immunological procedures for sex-differentiation of mammalian cells, including embryonic cells, sperm cells, epidermal cells, and fibroblast cells.

According to the practice of the present invention, a tumor cell line is produced using a standard immunological technique described in Oi and Herzenberg, "Immunoglobulin Producing Hybrid," supra. Spleen cells from female mice, hyperimmunized with injections of male mouse spleen cells, are fused with a mouse myeloma cell line in the presence of a chemical fusogen. A selected hybridoma cell cloned to propagate the cell line ATCC HB8116 produces an antibody in its growth supernatant which has highly specific anti-H-Y antibody action. This antibody, named "Hyclonalan," shows specific attraction for the H-Y antigen on male mammalian cells in various immunological procedures including an epidermal cell cytotoxicity assay, an embryo cytotoxicity assay, and a radio-immuno binding assay.

In immunological procedures to separate male from female embryos, Hyclonalan, in the presence of complement, demonstrates cytolytic effect on male cells, and no effect on female cells. The cytolysis of cells on the male embryos is microscopically observable, thereby enabling differentiation of the embryos into male and female pools.

Immunoselection techniques utilizing the monoclonal antibody of the present invention are also useful in the identification and separation of male from female epidermal and fibroblast cells, and in the detection of human sex chromosome abnormalities.

Additionally, Hyclonalan in immunological techniques for identification and separation of X- from Y-bearing spermatozoa is at least as effective as the antiserum disclosed in Bryant. U.S. Pat. No. 4,191,749.

Other aspects and advantages of the present invention will become apparent upon consideration of the following detailed description.

DETAILED DESCRIPTION

In the procedure for production of cell line ATCC HB8116, female mice of strain C57BL/6 (B6) (Jackson Laboratory) were hyperimmunized to the H-Y antigen by inoculating intraperitoneally with $2.5 \times 10^7$ B6 male spleen cells every two weeks for fourteen weeks. Three days prior to removal of the spleens from the females, they were given a tail vein boost of $5.0 \times 10^7$ B6 male spleen cells. Spleen cells removed from these females comprised the immune donor spleen cells for practice of the procedure of Oi and Herzenberg, supra. The parental myeloma cell line used in the present invention was the NS-1 cell line (P3-NS1-1, Cell Distribution Center, Salk Institute). Procedures for preparing and maintaining the NS-1 myeloma cell line are also disclosed in the Oi and Herzenberg publication.

Briefly, fusion of the NS-1 myeloma cells and the B6 immune spleen cells occured in the presence of the fusogen, polyethylene glycol 1500 (BOH Chemicals). Cell membranes fused and initially surrounded a common cytoplasm with two or more nuclei. Several days after that event, the nuclei fused and became capable of synchronous mitosis. As these fused cells divided, a variable number of chromosomes of both fused partners were lost until the hybrid cell line stabilized. Selection of NS-1:spleen cell hybrids from the fusion which also produces NS-1:NS-1 and spleen:spleen cell hybrids was accomplished by culturing the fusion mixture in hypoxanthine-aminopterin-thymidine (HAT) medium for two weeks. HAT medium prevented NS-1:NS-1 hybrids from growing. The spleen:spleen cell hybrids generally died after two weeks in culture. Thus the HAT medium allowed growth of only the NS-1:spleen hybrid cells.

After the two weeks in HAT medium, the NS-1:spleen cell hybrids were transferred to RPMI Growth Medium for continuous cultured growth. "RPMI Growth Medium" designates a medium composed of RPMI Medium (Gibco) supplemented with 10% Fetal Calf Serum (Sterile Systems), 1% Penicillin-Streptomycin (Gibco), 1% Essential Amino Acids (Gibco), 1% Glutamine (Gibco), and 1% Sodium Pyruvate (Gibco). After approximately two more weeks of cell growth, the supernates of cultures were individually harvested and tested in undiluted form for antibody activity.

After finding antibody activity in individual cell cultures, the cells were cloned by transfer into 1 milliliter cultures in culture plates using BALB/c thymocytes as feeder cells. After one week, the supernate of each culture was retested for antibody activity. Positive cultures were then cloned by limiting dilution in RPMI Growth Medium in microtiter wells containing $10^5$ BALB/c thymocytes and splenocytes as the feeder layer. Once these dilutions in RPMI Growth Medium were tested for antibody production, positive clones were transferred into RPMI Growth Medium in larger flasks.

Following these procedures, cell line ATCC HB8116 was found to produce a specific anti-H-Y monoclonal antibody in its supernate. Generation of Hyclonalan-containing supernate using ATCC HB8116 is accomplished by continuous cultured growth in RPMI Growth Medium at 37° C. in air. Optimal recovery of Hyclonalan in supernate when ATCC HB8116 is grown in RPMI Growth Medium is presently achieved when the concentration is $2 \times 10^6$ cells per milliliter.

Alternatively Hyclonalan can be obtained by the ascites method. In this procedure, cells of ATCC HB8116 are injected into the peritoneal cavities of mice, which had received 1 milliliter of Pristane (Aldrich) two weeks before inoculating with $5 \times 10^6$ Hyclonalan cells. Pristane permits growth of tumor cells in an ascitic form within the peritoneal cavity. One day before inoculation the mice received an additional 1 milliliter of Pristane and a 500 R dose of X-irradiation, which permits cells to initially grow. Once the ascitic tumor cells grow, the mouse is sacrificed and the ascitic fluid containing the H-Y antibody is separated from the cells by centrifugation at 1000 rpm. While this procedure produces a smaller volume of Hyclonalan, it is a more concentrated antibody than that produced in tissue culture. Dilution of the ascites fluid Hyclonalan preparations before use therefore produces a comparable effect to undiluted tissue culture supernatant Hyclonalan preparations.

Assays and tests to determine Hyclonalan's physiological characteristics have revealed that the antibody, proteinaceous in nature, contains kappa light amino acid chains, and is able to lyse cells in the presence of complement. A characteristic unexpected in light of the work of other experimenters on H-Y monoclonal antibody is that Hyclonalan does not bind Protein A. (See, Koo, et al., supra.)

The following examples illustrate immunological assays on the monoclonal antibody of the present invention, and more specifically relate to assays evidencing Hyclonalan's specificity for the H-Y antigen on mice epidermal cells and human fibroblast cells, Hyclonalan's kappa light chain constituency, Hyclonalan's cytotoxic characteristics, and use of its cytotoxicity in differentiating embryonic cells by gender.

EXAMPLE 1

Cytotoxicity Test on Mouse Epidermal Cells

To determine the specificity of Hyclonalan for the male cell surface antigen, H-Y, and to determine the antibody's cytotoxic (cell lysis) activity in the presence of complement, an assay was performed by a colleague of the inventor (Mark Shapiro, the University of Michigan School of Medicine, Ann Arbor, Mich., 1981). The assay incubated male and female mouse epidermal cells with Hyclonalan and complement. The cytotoxic index measures the percentage of cells lysed by exposure to Hyclonalan and complement. The greater the index, the greater the number of cells lysed.

TABLE I

| Treatment | Cytotoxic Index |
| --- | --- |
| Male cells incubated with Hyclonalan and complement | 0.17 |
| Male cells incubated with Hyclonalan (previously absorbed with male cells without complement), and complement | 0.02 |
| Male cells incubated with Hyclonalan (previously absorbed with female cells without complement), and complement | 0.16 |

These results show that when male cells are incubated with Hyclonalan in the presence of complement, a high degree of cytotoxicity is observed. When male cells were incubated with Hyclonalan alone, the H-Y activity was removed, so that other male cells incubated with the re-collected Hyclonalan in the presence of complement demonstrated little cytotoxic effect, indicated by an index of 0.02. Incubation of female cells (which do not contain the H-Y antigen) in Hyclonalan alone did not decrease the cytoxic activity. Thus when male cells were incubated with the re-collected Hyclonalan in the presence of complement, a high cytotoxic index was again observed, indicating that the antibody Hyclonalan is specific for the male surface antigen H-Y. This assay also revealed the physiologic characteristic of Hyclonalan as a "complement binding" or cytotoxic antibody.

EXAMPLE 2

Radio-Immuno-Binding Assay on Human Fibroblast Cells

This example relates to immunological procedures evidencing the anti-H-Y specificity of Hyclonalan and its physiological composition of kappa light amino acid chains. The procedure was performed by a colleague of the inventor (Jeanne Meck, The University of Miami, Mailman Center for Child Development, Miami, Fla., 1981).

A series of microtiter plate wells are filled with $1 \times 10^5$ human male and female fibroblast cells which are added to the wells in 200 lambda volumes, separated by cell gender. The cells are cultured at 37° C. for 24±2 hours.

Next, the culture medium is removed from the attached cells and the plates are left to air dry for 10–15 minutes. Then the cells are fixed by adding 10% neutral formalin to each well for at least 15 minutes. After removing the formalin, the cells are washed three times with phosphate buffered saline (pH 7.2). Then 2% bovine serum albumin in phosphate buffered saline is added to each well. The plates are incubated at 37° C. for 2 hours and the liquid is removed.

Hyclonalan supernatant in a 20 lambda volume diluted 1:3 and 1:6, as indicated in Table II, is added to each well containing the cells and is incubated for 1½ hours at 37° C. The wells are then washed six times with phosphate buffered saline to remove excess Hyclonalan.

Rabbit-anti-mouse kappa antibody (Bionetics), purified for the Immunoglobulin G fraction on a DE52 DEAE cellulose column (Whatman), is iodinated with radioactive iodine$^{125}$ and then added to the wells in 20 to 30 lambda volumes diluted in phosphate buffered saline and 2% bovine serum albumin. This provides approximately $5 \times 10^4$ to $50 \times 10^4$ counts per well. Following incubation for two hours at room temperature, the wells are washed six times with phosphate buffered saline to remove excess radioactive rabbit-anti-mouse antibody. The wells are then allowed to dry before being counted under a radioactivity counter.

This second labelled antibody, rabbit antimouse kappa antibody, will bind with any Hyclonalan in the plates. Because Hyclonalan is mouse-derived, it functions as an antigen to rabbit anti-mouse antibody. The amount of radioactivity, measured in counts per minute, indicates the comparative amounts of $I^{125}$-rabbit-anti-mouse antibody:Hyclonalan:cell surface antigen complexes found in the plates.

The results in Table II indicate the presence of significant amounts of Hyclonalan in the wells containing the male cells, compared to the female cells, which emit counts equal to the background counts caused by the attachment of the proteinaceous antibody Hyclonalan to the plastic wells.

This assay also indicates that Hyclonalan is formed of the kappa light amino acid chains, since it complexed with the labelled anti-kappa antibody.

TABLE II

| No. of $^{125}$I Counts Added | Dilution of Anti-H-Y Supernatant | $^{125}$I-bound cpm Male | Female/Background |
|---|---|---|---|
| Experiment 1: | | | |
| 500,000 cpm | 1:3 | 2305 | 1148 |
| 300,000 cpm | 1:3 | 1155 | 576 |
| 150,000 cpm | 1:3 | 729 | 333 |
| 50,000 cpm | 1:3 | 262 | 174 |
| 500,000 cpm | 1:6 | 2734 | 1558 |
| 300,000 cpm | 1:6 | 1355 | 759 |
| 150,000 cpm | 1:6 | 686 | 459 |
| 50,000 cpm | 1:6 | 340 | 226 |
| Experiment 2: | | | |
| 300,000 cpm | 1:3 | 2066 | 796 |

This experimenter indicated that these results show significantly greater male cell differentiation than any other monoclonal anti-H-Y antibody which she has subjected to the same assay. For example, the monoclonal H-Y antibody preparation of Koo, et al., supra, when subjected to this assay by the same experimenter, showed no difference in counts between wells containing male cells and wells containing female cells. Use of Hyclonalan in this assay has also indicated significant differences for comparative purposes in human fibroblast cells from humans with genetic abnormalities in their sex chromosomes, i.e., XX males.

EXAMPLE 3

Embryo Cytotoxicity Assay

This example relates to use of Hyclonalan in the immuno-selection of mouse 8-cell embryos and bovine 32- to 64-cell embryos. The procedures involved in this assay which demonstrates the complement-binding capacity of Hyclonalan as well as its use in a sex-immunoselection method for mammalian embryos are described in Krco, C. J., and Goldberg, E. H., "H-Y (Male) Antigen. Detection on Eight-Cell Mouse Embryos," Science, 193: 1134–1135 (1976), with the substitution of a monoclonal anti-H-Y antibody, Hyclonalan, for anti-H-Y serum.

Mouse embryos, desirably at the 8-cell stage, and bovine embryos at the 32- to 64-cell stage are flushed from the oviducts of the respective donors and pooled in Whitten's medium (prepared by the inventor as disclosed in Krco, et al., supra) containing 0.3% bovine serum albumin (Miles Laboratories). Loosening and cracking of the zona pellucida from the embryos is accomplished by treatment with 1% pronase, followed by repeated pipetting through a micropipet.

Following washing with bovine serum albumin supplemented Whitten's medium, the embryos designated as "experimental" and "Hyclonalan contol" are incubated in the presence of Hyclonalan for 15 minutes at 37° C. in a 5% $CO_2$ and 95% air incubator, humidified atmosphere. The "complement control" embryos are incubated only in the complement source, normal guinea pig serum (Gibco) diluted 1:4 in Whitten's Medium. The "antisera control" embryos are incubated in the presence of the H-Y antisera for 15 minutes at 37° C. in a 5% $CO_2$ and 95% air incubation humidified atmosphere. All embryos are then rewashed in Whitten's medium supplemented with bovine serum albumin. The "experimental" embryos are then transferred to guinea pig serum (Gibco) diluted 1:2 in Whitten's medium for another 15-minute incubation under identical conditions.

Once the excess complement is removed by another washing with Whitten's medium supplemented with bovine serum albumin, all embryos are observed by light microscopy. If one or more blastomeres in the "experimental" embryos are lysed, the embryo is positive for the H-Y antigen, and is therefore male. "Experimental" embryos demonstrating no lysis are female.

A. Mouse Embryo Results

At the present time, approximately one hundred mouse embryos have been subjected to this assay. A 50% cytolysis rate has been demonstrated, which correlates well with the naturally-occurring ratio of male:female embryos. Subsequent implantations of surviving mice embryos have produced female mice.

B. Bovine Embryo Results

This asay was performed on twenty-five bovine embryos: 10 formed the "experimental" group, 4 formed the "complement control" group, 3 were the "Hyclonalan controls", and 8 were the "antisera controls". The results are shown in tabular form below:

TABLE III

| Treatment | Number of Embryos | |
|---|---|---|
|  | Damaged | Undamaged |
| Complement alone | 0 | 4 |
| Hyclonalan alone | 0 | 3 |
| H-Y specific antisera plus complement | 4 | 4 |
| Hyclonalan plus complement | 5 | 5 |

To ascertain whether the undamaged embryos remained viable, they were cultured for 24 hours. Eight of the nine undamaged embryos went on to the blastocyst stage after culture.

Numerous modifications and variations in the practice of the present invention are expected to occur to those skilled in the art upon consideration of the foregoing description of the presently-preferred embodiments thereof. As one example, it may be understood that the monoclonal antibody claimed herein may be employed in various immunological procedures for the identification and separation of male cells from female cells, including traditional assays such as ELISAs. It is further expected that it would be possible to "tag" the monoclonal antibody with radioactive or fluorescent molecules to enhance such immunological identification. Consequently, only such limitations should be placed upon the scope of the invention as appear in the appended claims.

What is claimed is:

1. A hybridoma cell line, ATCC HB8166, that produces a monoclonal antibody having specific binding affinity to H-Y antigen.

2. A monoclonal antibody, Hyclonalan, produced by hybridoma cell line ATCC HB8116 and having selective binding affinity to H-Y antigen.

3. An immunological procedure for the identification and separation of male mammalian cells from female mammalian cells comprising:
   (a) contacting a mixture of said male and female cells with the monoclonal antibody, Hyclonalan, that has specific binding affinity to H-Y antigen and is produced by hybridoma cell line ATCC HB8116;
   (b) allowing a selective immunological reaction to occur between said male cells and Hyclonalan resulting in an antibody-male cell complex; and
   (c) detecting said complex and separating said female cells from said complex.

4. The procedure recited in claim 3 wherein said cells identified and separated are selected from the group consisting of mammalian spermatozoan cells and mammalian embryo cells.

5. The procedure recited in claim 3 wherein said detecting and separating step comprises lysing said male cells complexed with Hyclonalan in the presence of a source of complement.

6. The improvement recited in claim 5 wherein said complement source is normal guinea pig serum.

7. An immunological procedure for the identification and separation of male bovine embryos from female bovine embryos comprising:
   (a) contacting a mixture of said male and female embryos with the monoclonal antibody Hyclonalan, that has specific binding affinity to H-Y antigen and is produced by hybridoma cell line ATCC HB8116;
   (b) allowing a selective immunological reaction to occur between said male embryos and Hyclonalan resulting in an antibody-male embryo complex; and
   (c) detecting said complex and separating said female embryos from said complex.

8. The procedure recited in claim 7 wherein said bovine embryos treated are at the 32-cell stage.

9. The procedure recited in claim 7 further comprising reimplanting one or more sex-identified embryos into the uterus of a surrogate for development and birth of a calf of the desired gender.

10. The procedure recited in claim 7 further comprising incubating said embryos with a source of complement after said embryos are treated wity Hyclonalan.

11. The procedure recited in claim 10 wherein said detecting and separating step comprises identifying male embryos by the immunological effect of cytolysis of male cells of said male embryos.

12. An immunological procedure performed on human fibroblast cells for the detection of genetic abnormalities involving expression of the Y chromosome or a fragment thereof comprising:
   (a) contacting said cells with the monoclonal antibody, Hyclonalan, produced by hybridoma cell line ATCC HB8116 and having specific binding affinity to H-Y antigen present on the surface of cells expressing the Y chromosome or a fragment thereof;
   (b) allowing a selective immunological reaction to occur between said cells and Hyclonalan resulting in an antibody-cell complex; and
   (c) detecting and separating said cells expressing the Y chromosome of a fragment thereof from cells lacking said expression.

* * * * *